United States Patent
Meloul et al.

[11] Patent Number: 5,806,551
[45] Date of Patent: Sep. 15, 1998

[54] AUTOMATIC FLUID CONTROL VALVE

[75] Inventors: Raphael F. Meloul, Atlanta; Jonathan J. Rosen, Alpharetta, both of Ga.

[73] Assignee: Novoste Corporation, Alpharetta, Ga.

[21] Appl. No.: 409,756

[22] Filed: Mar. 24, 1995

Related U.S. Application Data

[63] Continuation-in-part of Ser. No. 154,944, Nov. 19, 1993, Pat. No. 5,529,278, and Ser. No. 217,672, Mar. 25, 1994, Pat. No. 5,462,255.

[51] Int. Cl.⁶ .................................................. F16L 37/28
[52] U.S. Cl. ..................... 137/15; 251/149.1; 251/212; 604/256; 604/905
[58] Field of Search .................... 604/256, 905; 251/149.1, 1.1, 212; 137/15

[56] References Cited

U.S. PATENT DOCUMENTS

| | | | |
|---|---|---|---|
| 2,832,338 | 10/1958 | Ryan | 128/214 |
| 3,861,388 | 1/1975 | Vaughn | 128/214 R |
| 4,112,944 | 9/1978 | Williams | 128/346 |
| 4,332,369 | 6/1982 | Gordon et al. | 251/114 |
| 4,432,767 | 2/1984 | Lobdell et al. | 604/86 |
| 4,535,820 | 8/1985 | Raines | 137/854 |
| 4,798,594 | 1/1989 | Hillstead | 604/256 |
| 4,834,716 | 5/1989 | Ogle, II | 604/192 |
| 4,878,897 | 11/1989 | Katzin | 604/86 |
| 4,915,687 | 4/1990 | Sivert | 604/83 |
| 4,946,445 | 8/1990 | Lynn | 604/192 |
| 5,061,253 | 10/1991 | Yoshida | 604/246 |
| 5,139,483 | 8/1992 | Ryan | 604/905 |
| 5,163,922 | 11/1992 | McElveen, Jr. et al. | 251/149.1 |
| 5,188,629 | 2/1993 | Shimoda | 604/905 |
| 5,203,775 | 4/1993 | Frank et al. | 604/256 |
| 5,215,538 | 6/1993 | Larkin | 251/149.1 |
| 5,226,898 | 7/1993 | Gross | 604/243 |
| 5,242,432 | 9/1993 | DeFrank | 604/284 |
| 5,279,571 | 1/1994 | Larkin | 604/167 |
| 5,281,206 | 1/1994 | Lopez | 604/283 |
| 5,350,363 | 9/1994 | Goode et al. | 604/256 |
| 5,360,413 | 11/1994 | Leason et al. | 604/249 |
| 5,509,433 | 4/1996 | Paradis | 251/149.1 |

*Primary Examiner*—A. Michael Chambers
*Attorney, Agent, or Firm*—Bernstein & Associates

[57] ABSTRACT

An automatic fluid control having a first and second tube members and a slidable valve element capable of moving from a sealed closed position to an open position permitting fluid passage therethrough. In a preferred first embodiment, the elastomeric valve element is slidingly received with a passageway in the first tube. The valve element has a flange portion containing a plurality of slits that, when inverted and stretched, permit fluid to pass therethrough, but when closed, are in contact with the inner wall of the first tube and prevents fluid from passing therethrough. The valve element also can have a rigid plug attached within an opening in the top surface to present a preferably non-deformable contact point for a male luer tip, which, when pressed downward on the valve element, breaks a seal between the valve element and the first tube inner wall. In a second embodiment a toroidal shaped valve portion selectively forms a seal over a pin extending axially from the second tube member, the pin having a plurality of grooves in its surface to permit passage of fluid when the seal created by the valve element is broken. In a third embodiment, a valve element maintains a seal against a pin extending from the base of the second tube member and having a plurality of grooves. When the valve element is urged downward against the upward force of a spring, the pin grooves permit fluid flow through the second tube member.

35 Claims, 13 Drawing Sheets

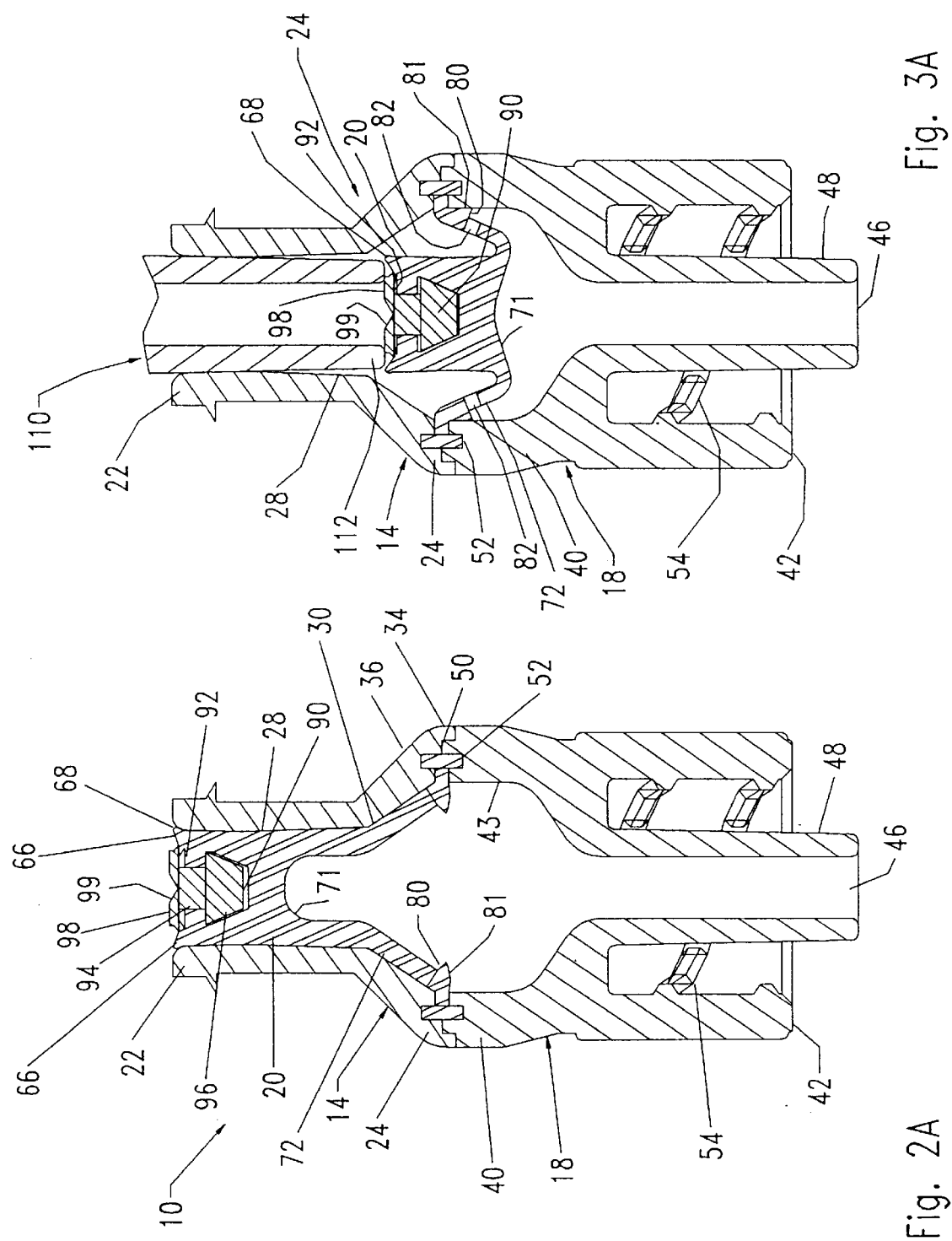

DETAIL OF TOP PORTION
OF VALVE ELEMENT

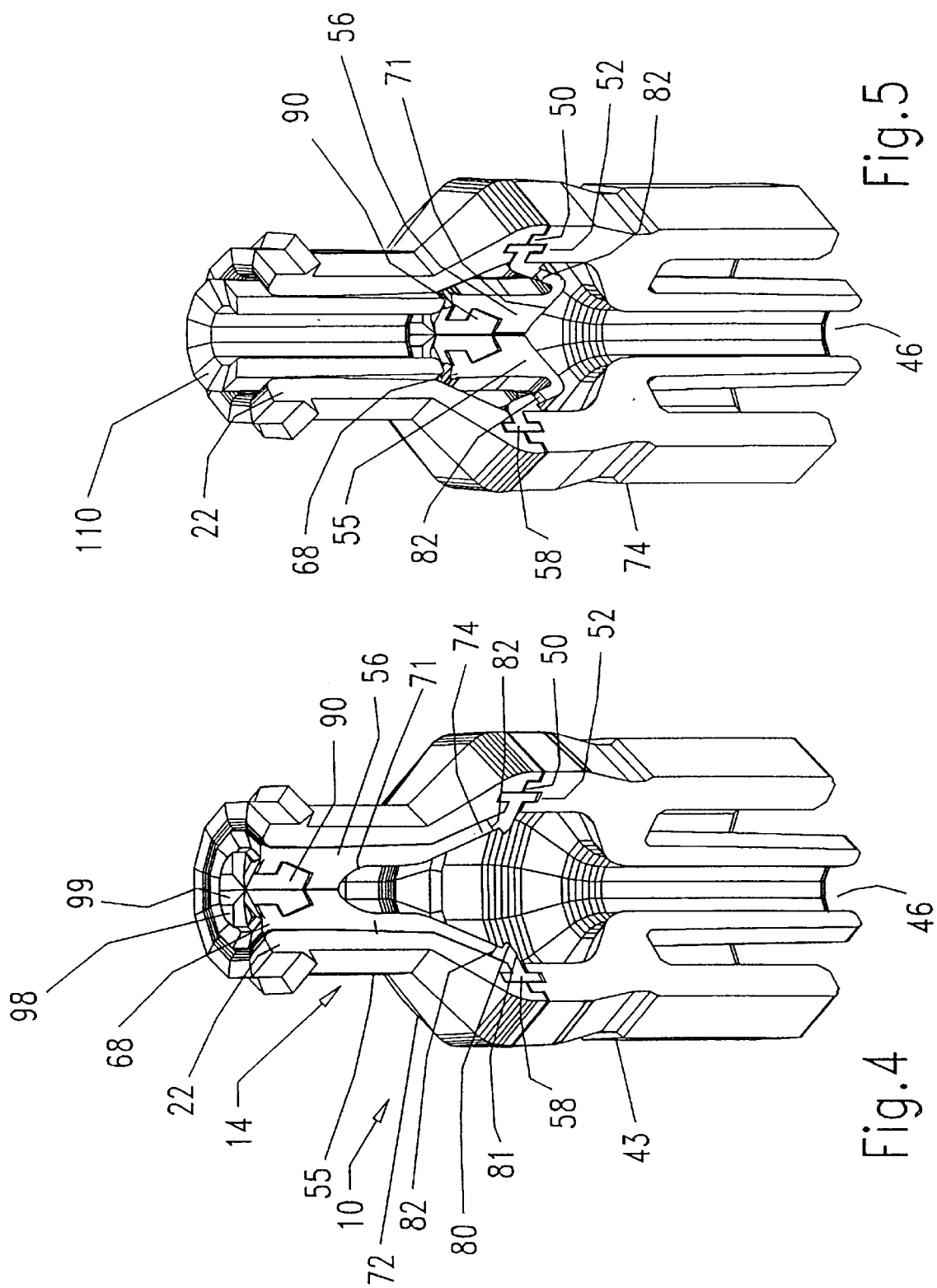

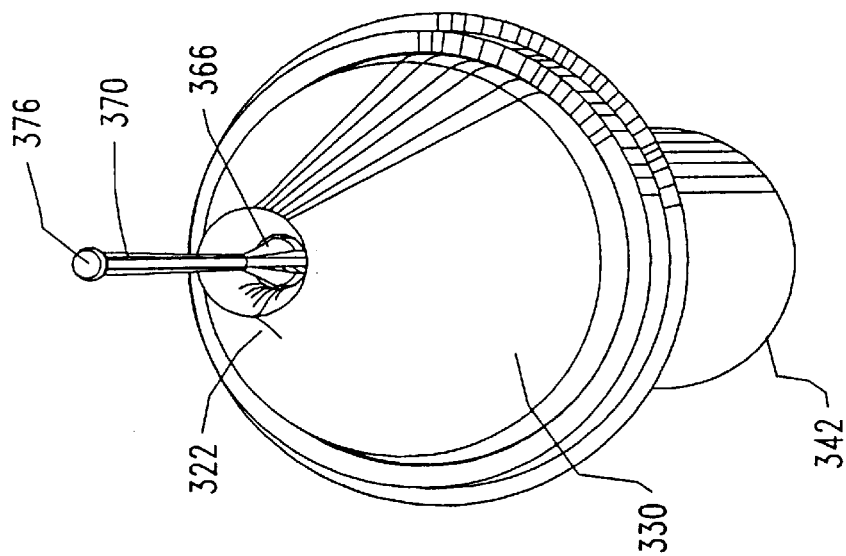
Fig. 10-C
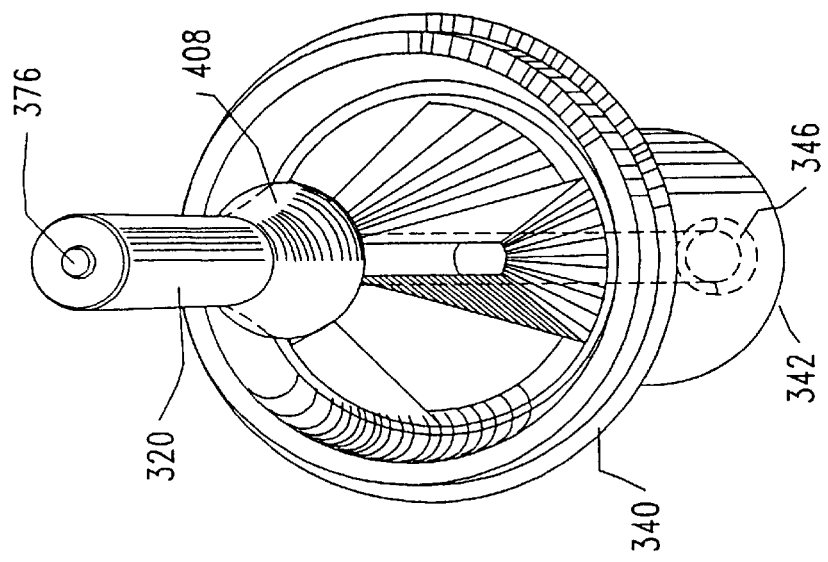
Fig. 10-B
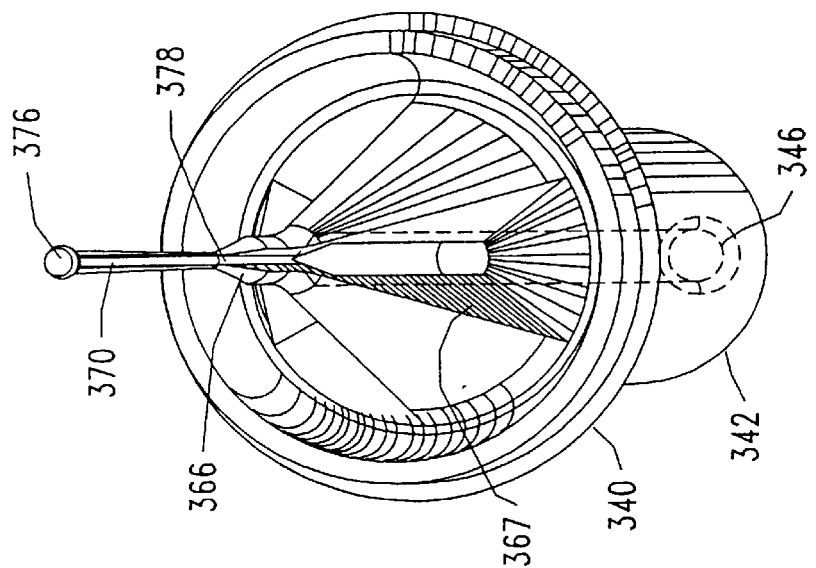
Fig. 10-A

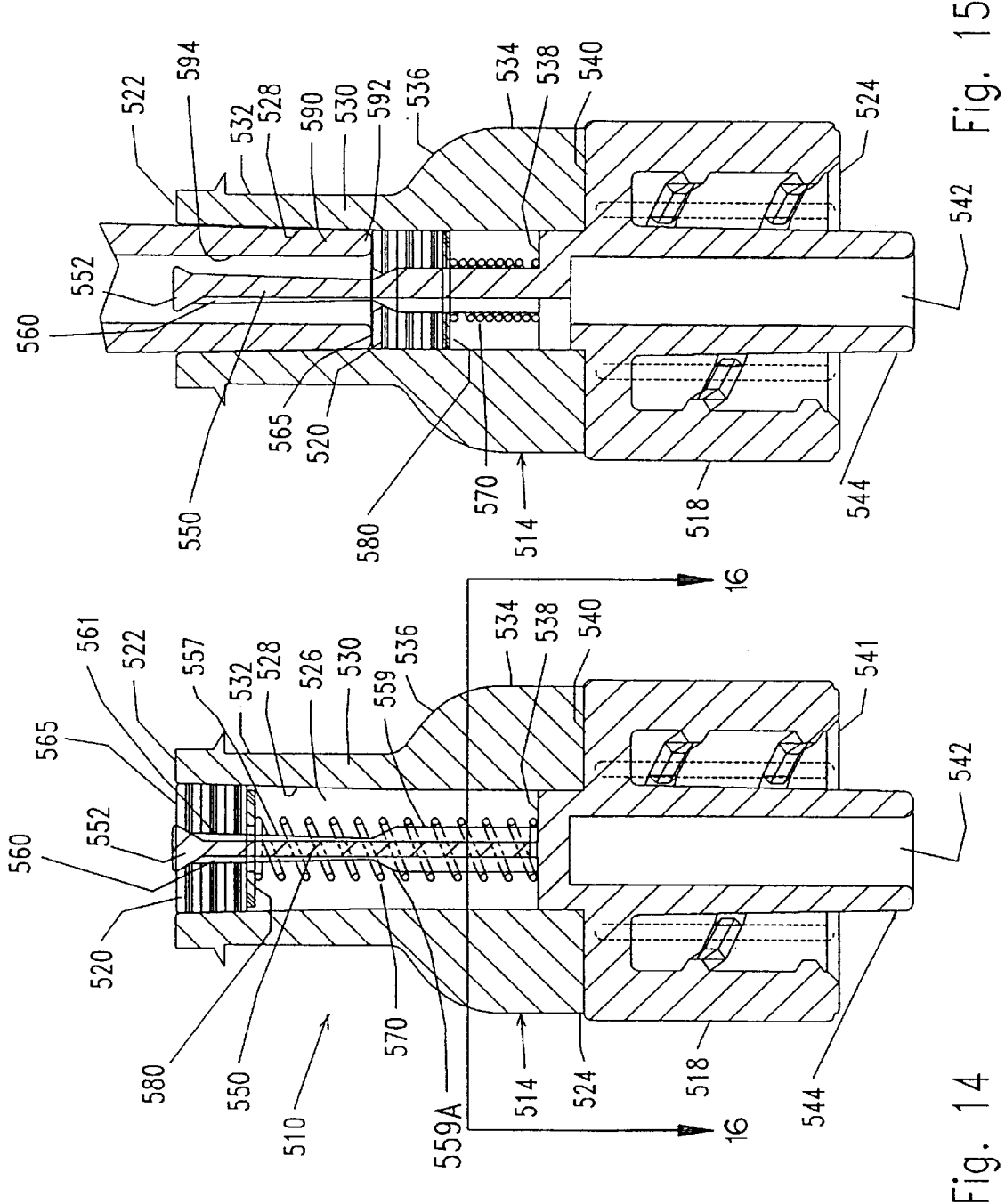

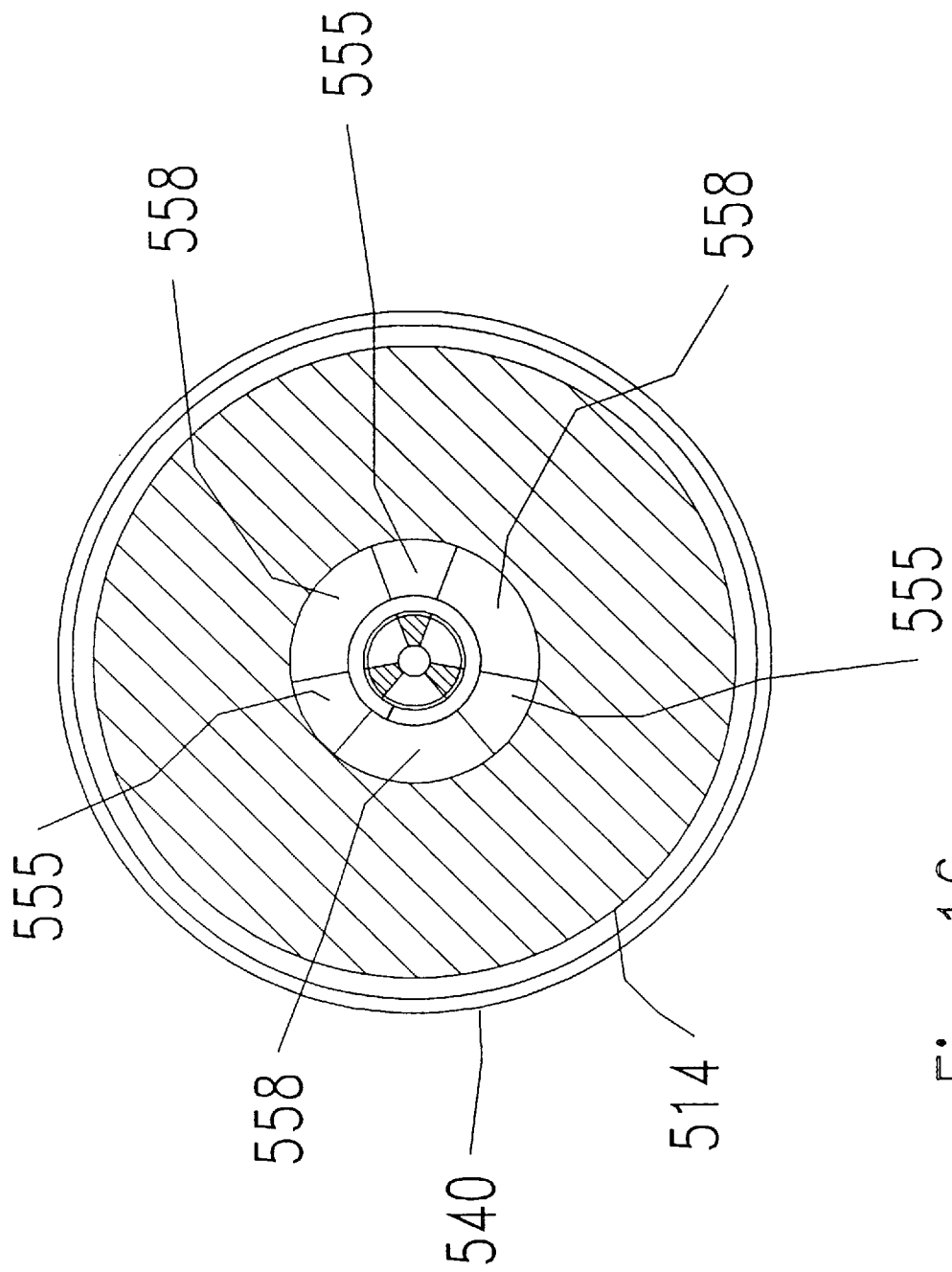

AUTOMATIC FLUID CONTROL VALVE

CROSS-REFERENCE TO RELATED APPLICATIONS

This application is a continuation-in-part of applications Ser. No. 08/154,944 now U.S. Pat. No. 5,529,278, filed Nov. 19, 1993, and Ser. No. 08/217,672 now U.S Pat. No. 5,462,255, filed Mar. 25, 1994, which are incorporated by reference herein in their entirety.

FIELD OF THE INVENTION

The present invention relates to a fluid control valve, and more particularly to an automatic valve having a valve element maintained in slidable engagement with a tube member.

BACKGROUND OF THE INVENTION

Flow control valves for restricting or permitting fluid flow come in many shapes and sizes, and are made of a wide variety of materials depending on their intended use.

Typically, flow control valves such as butterfly valves and gate valves are used to control flow of fluid by moving a mechanical member into and out of the flow path to partially or completely block the flow path. Other types of valves, for example roller clamps used in medical intravenous apparatus, control flow by pinching the plastic tubing through which the fluid flows. Still other types of valves operate by controlling the length of the flow path, and therefore the resistance to flow, through the valve.

Despite the wide variety of valves that have been used heretofore, there is a continuing need for improved flow control valves that have cost, ease of use, functional, and other advantages compared to prior flow control valves. A significant need exists for a valve that contains a minimum number of parts, and that those parts form a sealed access port which can be effectively cleaned by an alcohol wipe. There is also a need for a flow control valve that has minimal dead space to minimize the area in which air can become entrapped; one that is easily purged of air, and one that has a minimal priming volume.

DESCRIPTION OF THE PRIOR ART

Prior art valves have the tendency to create a pressure wave when a needle or syringe tip is introduced into the valve because the valve seal must displace a significant volume of fluid or air in order to move and break the seal at the valve seat. This pressure wave can introduce a pressure wave into the bloodstream downstream from the valve. Such valves commonly have only a fully closed or fully open position, with little ability to control the fluid volume displaced by the introduction or withdrawal of a needle or syringe tip. Certain patients, particularly neonates, young children, and people with blood pressure disorders, are very sensitive to fluid pressure changes in the bloodstream. Prior art valves can introduce a back pressure volume wave into the bloodstream of these patients, potentially causing fluid overload and pressure receptor overload, and consequent injury. It would be desirable to have a valve that had a minimized volume of fluid or air that was displaced. Additionally, it would be desirable to have a valve that allowed a user to withdraw an amount of fluid while inserting a needle or to inject an amount of fluid when withdrawing a needle in order to balance out the fluid pressure and volume in the bloodstream.

U.S. Pat. No. 5,215,538, issued to Larkin discloses an in-line valve having a mated pair of tube members and a valve member comprising an elastomeric membrane having flow holes therein and a projection extending from the membrane. The membrane is secured across the passageway between the two tube members by a rim which engages the ends of the tube members when mated. The membrane is "tensioned across and in sealing engagement with the annular valve seat." The projection is urged downward when a connector engages the projection and the valve seal is broken, permitting fluid flow.

The inlet tube of Larkin must be of a certain minimum depth to engage and lock with a standard luer taper connector. The projection associated with the valve membrane is inserted during assembly into the inlet tube. Even with full insertion there remains an empty well that is exposed to the air and which can collect dirt and contaminants. This well cannot easily be cleaned. If the projection were modified to be long enough to fill the inlet tube, when a connector was inserted the amount of downward displacement of the projection would likely cause the valve membrane to rupture. Therefore is not likely that Larkin could be adapted to remedy this deficiency.

Larkin utilizes a valve member in which the sealing surface is also the elastomeric member. In other words, the seal itself must stretch both laterally and axially. A problem with this type of design is that the deformation of the valve seal may not be even when the projection is moved downward to break the seal, resulting in possible fluid leakage around the membrane. Furthermore, the elastomeric membrane cannot be deformed axially significantly if it is to maintain the valve seal. It would be desirable to have a valve seal that does not require lateral deformation so as to ensure a proper fluid tight seal.

In Larkin, once the luer connector moves the projection downward even partially the valve seal is broken. Until the connector is locked into place there exists the possibility of fluid leakage back through the seal and the luer taper inlet tube to the inlet connector because there is no secondary seal anticipated that is maintained until the connector is locked in place. Where there is substantial back pressure this may result in contamination of the inlet fluid.

It would be desirable, then, to have a fluid control valve which would utilize a valve that is held in displaceable sealing engagement with a valve sealing surface and that would in a closed position completely fill the connector passageway so as to form a seal that would be cleanable by an alcohol wipe.

U.S. Pat. No. 5,360,413, issued to Leason et al. discloses a needleless access device having an elastic valve member sandwiched between two rigid tubes. Leason has a wiper seal as part of the valve element. As the valve element is forced downward or upward by a luer tip, the valve element acts as a plunger and the wiper seal creates a pressure wave that is undesirable. Additionally, the space between the wiper seal and the inner wall of the upper tube member can be a site for collection of contaminants. It would be desirable for a valve assembly to obviate the need for a wiper seal and eliminate the space between the valve element wall and the upper tube inner wall, yet would be sealed against contaminants and have a wipable top surface.

Additionally, Leason et al. has a significant dead space in the lower tube member which can trap air, which needs to be avoided when injecting fluid into a person. It would be desirable to have a valve assembly designed to eliminate the air trap dead space and to minimize the overall volume within the valve assembly.

SUMMARY OF THE INVENTION

The present invention generally provides an automatic fluid control valve having an upper and a lower rigid hollow tube members that can be matingly joined. A valve element mounted within the valve assembly can be slidingly moved within the upper tube member.

A first preferred embodiment of the present invention provides a first rigid tube member having a top, a bottom, a first portion containing a first inner wall defining a first passageway having a first diameter, and having a flared second portion extending axially from the first portion and containing a second inner wall defining a second passageway, and defining a primary valve sealing surface. A second rigid tube member has a top and a bottom, an inner passageway defined therein by an inner wall. The first and second tube members are capable of mating engagement with axial alignment, the bottom having a male luer connection defined therein.

An elastomeric cylindrical valve element assembly comprises a first portion having an outer wall, a top surface, the top surface having an aperture and a bore defined therein, the aperture having an inwardly projecting flange, the bore containing a beveled portion and a lip, and the top surface having an outwardly projecting flange capable of forming a seal with the first passageway of the first rigid tube member when inserted therein and when in a closed position; a rounded concave bottom surface; a tubular second portion extending downward from the first portion; a third portion extending downward from the second portion and flaring outward, the third portion angling outward at its edge and terminating in an annular lip, the third portion having an inwardly protruding annular boss, the third portion also having at least one opening defined therein for permitting fluid to selectively pass therethrough; and, a plug comprising a generally cylindrical tube of rigid material having a top surface, the top surface having at least one notch defined therein, a straight portion terminating in a lip and a beveled lower portion having a bottom, the plug being capable of being received within the aperture in the top surface and the bore of the valve element. The valve element can be maintained by the annular lip between the first tube member and the second tube member such that the valve element can be moved from a closed position in which fluid is prevented from passing through the valve assembly to an open position wherein fluid can pass through the at least one opening in the third portion of the valve element and through the second inner passageway in the second rigid tube member.

The valve is assembled by placing the valve element between the first and second tube members and maintained therebetween by the annular lip being received within a groove in the first tube member and a groove in the second tube member so that the valve element can slide within the first tube member. The first and second tube members can be sealed together, such as by sonic or heat welding, glue, or the like. In an alternative embodiment, shown in FIG. 6, the first and second tube members can be modified to snap fit together. FIG. 6 shows the first tube member 14 having a beveled lip "A" and the second tube member 18 having a snap-matable beveled lip "B." The beveled lips "A" and "B" can be snap-fit together to eliminate the gluing or welding process. It is also possible to add a gasket (not shown in FIG. 6) which would fit between the beveled lips to reduce the likelihood of leakage.

In the closed position the valve element present several points of seal to prevent fluid entry into the valve. The upper portion of the valve element and the outer flange on the upper surface thereof forms a seal with the inner wall of the first tube member. The flared portion of the valve element forms a seal with the flared inner wall of the lower portion of the first tube member. The slits are closed and prevent fluid from passing therethrough.

A method of operation comprises inserting a male luer tip into the first tube member by contacting the valve element. The luer tip presses down on the top surface of the plug, which causes the inner flange of the top surface to deform inward, drawing the outer flange of the top surface inward, which breaks the fluid seal. As soon as the fluid seal is broken, and prior to the valve element being in the completely open position, some fluid can flow down the valve walls and through the valve assembly. As the luer tip is urged downward the valve element moves downward and the flared portion inverts and stretches, thereby breaking the seal with the flared portion of the inner wall of the first tube member and opening the slits. Fluid can pass through the valve element and exit through the opening in the bottom of the second tube member. The inwardly protruding annular boss pivots and contacts the inner wall of the second tube member, thus preventing air from becoming trapped in the corner of the valve element and minimizing dead space.

When the male luer is removed, the valve element reverts back to its original shape due to its elastomeric shape memory, resealing the valve.

In a second embodiment of the present invention, an automatic fluid control valve comprises a first rigid tube member having a top, a bottom, a first portion containing a first inner wall defining a first passageway having a first diameter, the first tube member also having a second portion extending axially from the first portion and flaring outward, terminating in a lip. A second rigid tube member has a base portion, at least one fluid passageway defined in the base portion, at least two ribs extending upward from the base portion, the volume between the ribs defining a fluid passageway in communication with the at least one fluid passageway defined in the base portion, and a pin extending upward from the at least two ribs and having a proximal and a distal end, the pin having at least one longitudinal groove defined therein, the groove being in fluid communication with an inner passageway in the base portion, the distal end of the pin terminating in a protuberance. The first and second tube members are capable of mating engagement with axial alignment.

A valve element comprises a generally cylindrical elastic body having a top and a bottom and having an upper portion having a generally tapered outer wall and a tapered inner wall, a middle portion having a generally flared outer wall terminating in a toroidal shaped lower portion, the valve element having a fluid passageway defined axially therein sized to be able to slidingly receive the pin.

The valve of this embodiment is assembled as described generally in the first embodiment.

A method of operating the valve comprises contacting a male luer tip to the top surface of the valve element and pressing downward. As the valve element is urged downward, the seal formed between the protuberance and the beveled inner top wall of the valve element breaks, permitting a partial fluid flow from the luer tip through the grooves in the ribs and out the opening in the bottom of the second tube member. Concurrently, the pin becomes inserted in the luer. As the luer tip becomes fully inserted and engaged, the valve element is fully stretched, permitting a full flow of fluid through the grooves and out the bottom opening. As the luer is withdrawn, the valve element returns to its original shape, reforming the seals.

A third embodiment of the present invention provides an automatic fluid control valve, comprising: a rigid first tube member having a top, a bottom, a tapered inner wall defining a passageway; a rigid second tube member having an inner passageway defined therein, an inner base surface, a pin extending upward from the inner base surface and terminating in a protuberance having a beveled sidewall, the pin having a plurality of grooves defined therein spaced around the circumference thereof, the area between the ribs creating at least one groove capable of acting as a fluid passageway, and an outer base ring, the bottom of the first tube member being capable of mating engagement with axial alignment with the outer base ring of the second tube member. An elastomeric valve element comprises a generally cylindrically shaped tube having an aperture defined axially therein, a top surface, a bottom surface, an inner wall having a bevel around the inner wall of the top surface, and an outer wall, the valve element being capable of slidingly fitted on the pin, such that when the valve element is in a closed position the beveled top surface forms a seal with the beveled surface of the pin. The valve also comprises a washer abutting the bottom surface of the valve element and a spring placed under a compressive force against the valve element for maintaining an upwardly biased force against the bottom surface of the valve element.

The valve is assembled by placing the spring over the pin. The valve element and washer are then placed over the pin so that they compress the spring slightly and are urged up against the protuberance to form a fluid tight seal. The first tube member is then inserted over the valve element and the pin and joined to the outer lip of the second tube member. The first and second tube members are sealed.

A method of operation of this embodiment comprises contacting the valve element with a luer tip. The valve element is urged downward against the upward force of the spring, the seal is broken between the protuberance and the inner wall of the valve element, permitting a partial flow of fluid to occur through the grooves in the pin and through and out the bottom of the second tube member. When the luer is in its maximum downward/open position, the valve element deforms slightly and the diameter of the inner wall of the valve element increases, permitting a full flow of fluid through the grooves of the pin and out the bottom.

Accordingly, it is a principal object of the present invention to provide an automatic fluid control valve having a minimal number of parts.

It is a further object of the present invention to provide a valve that forms a sealed access port which is externally cleanable with an alcohol wipe.

It is another object of the present invention to provide a valve having a seal maintained by an elastic member associated with the valve.

It is yet another object of the present invention to provide a valve having an automatic positive seal in the closed position to prevent leakage of fluids in both directions.

It is still another object of the present invention to provide a valve having an elastomeric valve element capable of stretching and inverting from a closed position to an open position.

It is another object of the present invention to provide a valve having a reduced dead space to prevent air bubbles from being trapped in the valve.

It is yet another object of the present invention to provide a valve that does not have a wiper seal yet maintains, in the closed position, a barrier against contamination.

Other objects, features, and advantages of the present invention will become apparent upon reading the following detailed description of embodiments of the invention, when taken in conjunction with the accompanying drawings and the appended claims.

BRIEF DESCRIPTION OF THE DRAWINGS

The invention is illustrated in the drawings in which like reference characters designate the same or similar parts throughout the figures of which:

FIG. 2A shows a side elevation in cutaway of a first embodiment of the present invention with the valve element in the closed position.

FIG. 3A shows a side elevation in cutaway of a first embodiment of the present invention with the valve element in the open position.

FIG. 4 shows a perspective view in partial cutaway of a first embodiment of the present invention with the valve element in the closed position.

FIG. 5 shows a perspective view in partial cutaway of a first embodiment of the present invention with the valve element in the open position.

FIGS. 10A, B and C show top perspective views in partial cutaway of a second embodiment of the present invention.

FIG. 14 shows a side elevation in cutaway of a third embodiment of the present invention with the valve element in the closed position.

FIG. 15 shows a side elevation in cutaway of a third embodiment of the present invention with the valve element in the open position.

FIG. 16 shows a top view of a third embodiment of the present invention taken along line A—A of FIG. 14.

DESCRIPTION OF THE PREFERRED EMBODIMENTS

Figure 1A:
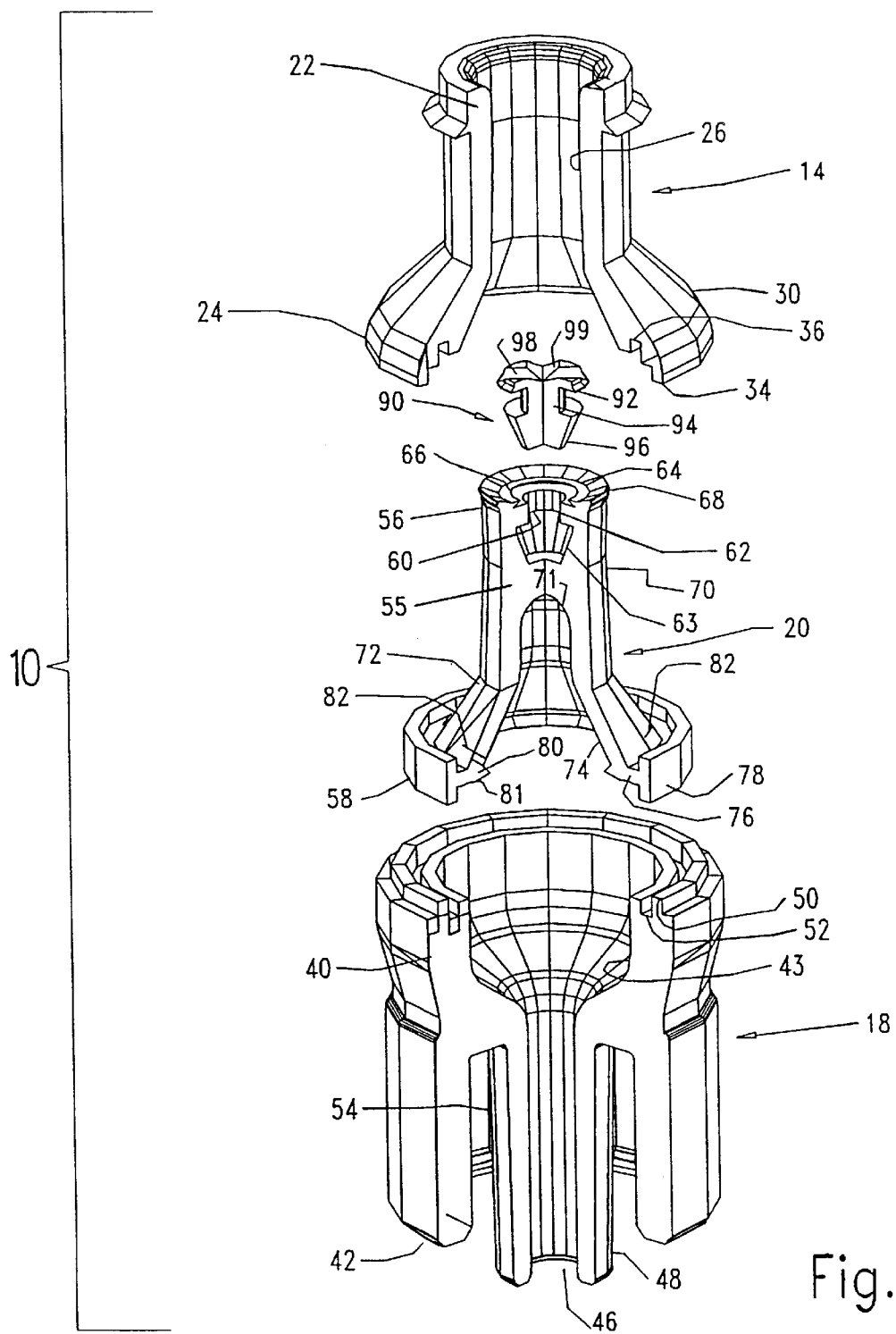
FIG. 1A shows an exploded perspective view in partial cutaway of a first embodiment of the present invention.

FIGS. 1–6 show a first embodiment of a valve assembly 10 of the present invention, which generally comprises valve body 12 which is made of a first tube member 14 and a second tube member 18. A valve element 20 is slidingly disposed within the valve body 12. The first and second tube members 14 and 18 are made of a rigid material, such as a polymeric or plastic material. Other materials can be used, such as metal or ceramic, but a polymeric material such as carbonate, acrylate, or other solvent resistant moldable material is preferred. For the purposes of the present disclosure the terms top, bottom, up and down, and the like, are used merely for convenience, and not limitation, when viewing the drawings with the first tube member 14 being positioned over the second tube member 18.

The first tube member 14 comprises a cylindrical housing having a first end 22 and a second end 24. The upper half (approximately) of the inner wall 26 of the first end 22 is sized as a tapered female luer bore and extends through a portion of the first end 22 forming a first passageway 28 (not shown). Preferably, the lower half of the inner wall 26 is sized to be a reverse luer taper, actually widening the diameter, so that the valve element 20 does not get stuck in the passageway 28 before returning to a completely closed position. Alternatively, the lower portion of the inner wall 26 can continue in a standard female luer taper. A second portion 30 of the first tube member 14 extends downward and widens gradually (forming a second passageway 32, not shown in the drawings) forming a primary valve sealing surface. The bottom end 24 terminates in a lip 34 and a groove 36.

The second tube member 18 comprises a cylindrical housing having a top end 40 and a bottom end 42 with a bore extending therethrough having an inner wall 43 defining a third passageway 44 (not shown) having a diameter substantially the same as the diameter of the second passageway 32. This diameter preferably tapers slightly toward the second end 42. The bottom end 42 has an opening 46 and can optionally have a male luer fitting 48 associated therewith and fluid communication with the passageway 46. The male luer fitting 48 can be connected to an external thread on a separate connector. Alternatively, the bottom end 42 can be adapted to be fitted to an integral part of a tubing in a Y-site, multiple manifold, or other configurations, as described in detail in the co-pending application. The top end 40 has a rim 50 and a groove 52.

Figure 1B:
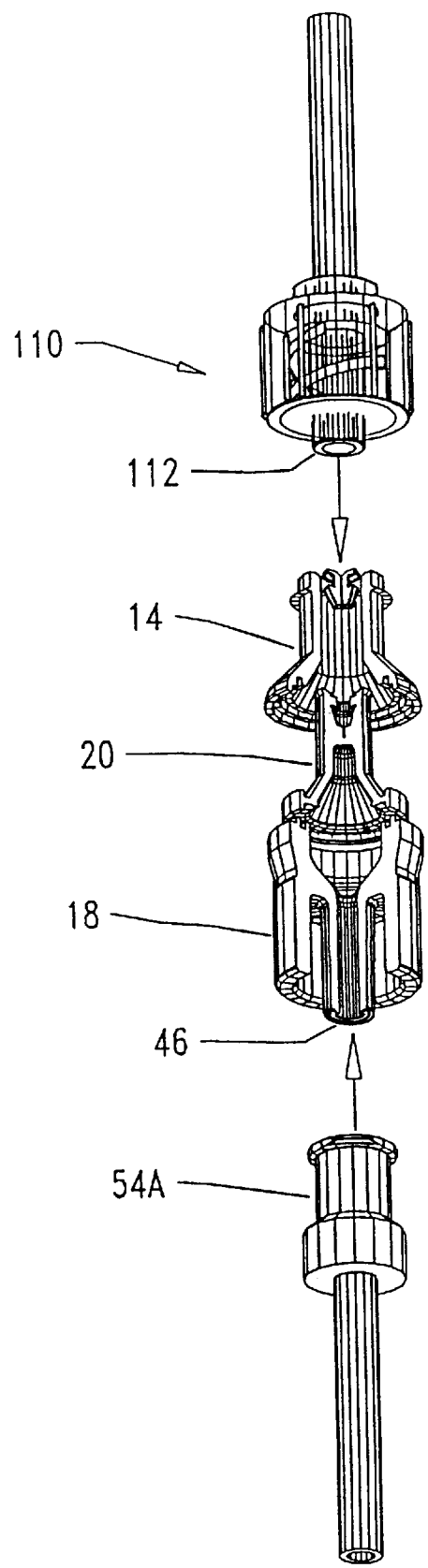
FIG. 1B shows an exploded perspective view in partial cutaway of a first embodiment of the present invention with a female and a male luer in proximity to the top and bottom ends of the valve.

As shown best in FIGS. 1A and 1B, an internal thread 54 projects inwardly from the circumference just below the bottom end 42, and is sized to be capable of mating with a female luer fitting 54A.

The first and second tube members 14 and 18 are made of a rigid, biologically inert material, such as but not limited to TEFLON®, ISOPLAST®, polycarbonate, or the like.

The valve element 20, as shown in greater detail in FIGS. 2B–3B, comprises an elastic deformable hollow structure having an upper portion 55 containing a top end 56 and also having a flared portion 72 and a bottom end 58. The top end 56 has an opening 60 defined by an inner wall 62, a portion of which is beveled, noted as element 63. A flange 64 is recessed within the wall 62 of the upper portion 55 and the top end surface 66. The recessed flange 64 is flexible and deformable, as described more fully hereinbelow in the operation of the apparatus. A projecting flange 68 projects annularly from the outer wall 70 of the top end 56. The outer wall 70 has a reverse luer taper along the lower part of the upper portion 55 and a standard luer taper along the lower part of the upper portion 55. The valve element 20 is preferably made of silicone rubber, C-Flex, or the like, but any suitable elastomeric material that is biologically inert, flexible and deformable can be used. The upper portion 55 has a rounded concave inner wall 71.

The flared portion 72 having an inner wall 74 extends downward from the upper portion 55 and terminates in an angled portion 76. A lip 78 extends both upward and downward from the angled portion 76. An angled inner-protruding annular boss 80 having an underside 81 extends from the inner wall 74 of the flared portion.

At least one slit 82 is disposed in the flared portion 72 and extends from the outer wall 70 to the inner wall 74. Preferably, a series of slits 82 are spaced around the flared portion 72. The slits 82 are elongated yet are closed when the valve element 20 is in the upper, or closed, position, as more fully described hereinbelow. When the valve element 20 is deformed into the open position, the slits 82 will be drawn open, permitting passage of fluid therethrough. Thus, it is preferable, although not mandatory, that the slits be perpendicular to the axis of the valve element 20, so that deformation in a downward axial manner will cause stretching of the flange portion 72 and opening of the slits 82. The slits 82 can be arranged in a ringlike arrangement, a grid, or randomly in the flared portion 72.

A plug 90 is made of a material less elastic than the valve element 20, and preferably a relatively rigid material, such as, but not limited to, ISOPLAST and polycarbonate. The plug 90 can be of various possible shapes. It is designed to be inserted into the opening 60 and maintained in position. It can be removably or permanently mounted in the opening 60. In a preferred embodiment, the plug 90 has a top portion 92, a straight portion 94 and a beveled lower portion 96. The top portion has a top surface 98 which has a notch 99, which prevents a seal from being formed on the top surface 98 when a male luer tip is engaged therewith, as will be described in more detail hereinbelow. Alternatively, rather than a notch, a series of ridges, bumps, dimples, grooves, grids or the like can be used to create a fluid access and prevent a seal from forming when a luer tip is contacted therewith. The plug 90 is sized to be received within the opening 60 in the mating inner wall 62 and 63, in a snap fit.

The plug 90 is important in the preferred embodiment because it provides a nondeformable, or minimally deformable, surface which a luer tip (as described in greater detail hereinbelow) can contact. If the surface of the top of the valve element were deformable, a male luer contacting the top surface would form a fluid tight seal, preventing fluid from passing into and through the valve assembly. Therefore, it is preferable that the plug present a nondeformable surface to permit fluid to pass through when the valve element is moved into the open position. Alternatively, it is possible that the plug 90 can be deformable, but there can be bumps or grooves on the top surface of the plug 90 which prevent a seal from forming.

Figure 6:
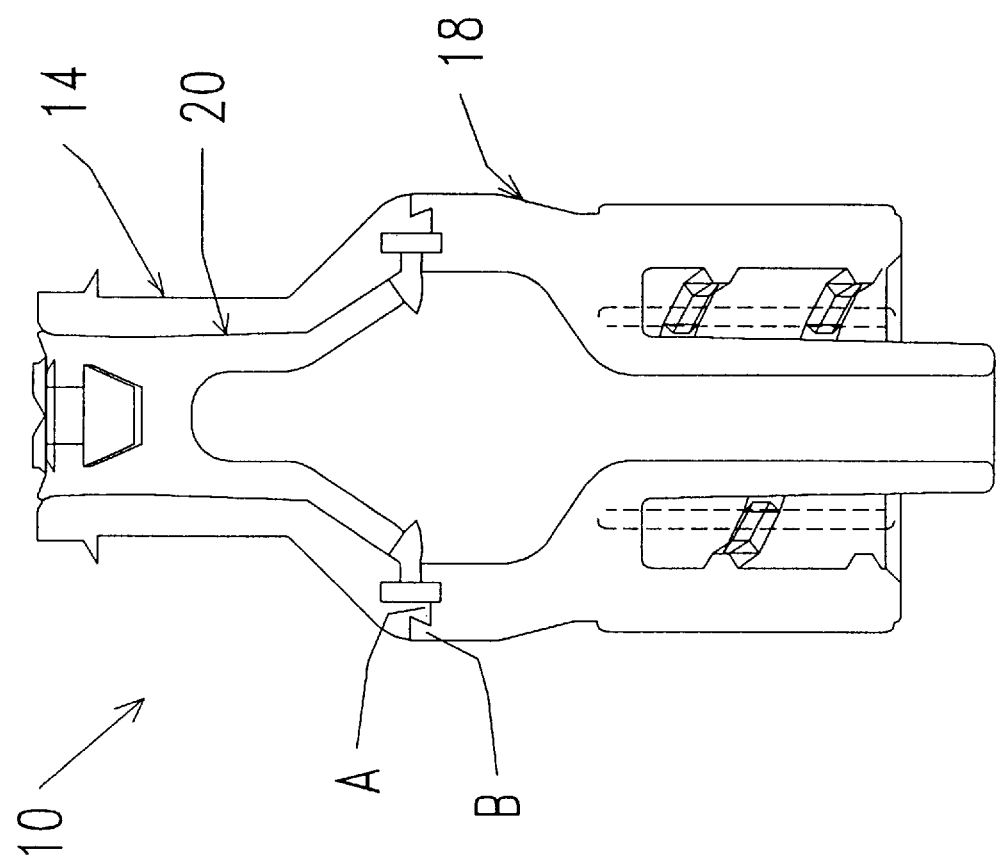
FIG. 6 shows a side elevation in cutaway of an alternative construction of the first embodiment of the present invention employing a snap fit means for engaging the first and second tube members.

To assemble the apparatus, the valve element is placed between the first tube 14 and the second tube 18, with the lip 78 sitting within the groove 52 in the second tube 18 and the groove 36 of the first tube 14. The contacting surfaces of the first and second tubes 14 and 18 are permanently attached to each other, such as by welding (sonically, heat or the like), gluing, or the like. It is to be understood that the present invention can be modified, as shown in FIG. 6, to be snap fit together. FIG. 6 shows the first tube member 14 having a beveled lip "A" and the second tube member 18 having a snap-matable beveled lip "B." The beveled lips "A" and "B" can be snap-fit together to eliminate the gluing or welding process. It is also possible to add a gasket (not shown in FIG. 6) which would fit between the beveled lips to reduce the likelihood of leakage.

When the valve assembly 10 is assembled, as shown in FIGS. 2A, 3A, 4 and 5, the top portion of the valve element 20 slidingly resides within the inner passageway 28 and the flange 68 forms a seal with the top end 22 to prevent fluid from passing therethrough. The slits 82 are closed and the outer wall of the flared portion 72 abuts the second passageway 32.

The method of operation can be understood by viewing FIGS. 4 and 5, which show the valve assembly 10 in a closed position prior to insertion of a male luer tip. At this point the projecting flange 68 acts as a seal against the upper portion of the inner wall 26 to prevent contaminants from entering the valve assembly 10. Additionally, the flared portion 72 is in contact with the inner wall 30 as an additional seal. Further, in the closed position, the slits 82 are closed as a further seal. FIGS. 3A and 4A and 5 show a male luer 110 inserted into the first passageway 28. The tip 112 of the luer is pressed downward on the valve element 20 by contacting the top surface 98 and the notch 99 of the plug 90. The notch 99 prevents a seal from forming between the top surface 98 and the luer tip 112, which would otherwise block the flow of fluid from the luer through the assembly 10. As the luer tip 112 is pressed downward the recessed flange 64 deforms and collapses, drawing the flange 68 in slightly and breaking the seal so as to permit the valve element 20 cylinder to slide downward without a seal being formed between the flange 68 and the inner wall 26. This is an advantage over previous designs, such as in the Leason patent, because the flange 68 does not form a "wiper seal" with the inner wall 26 from top to bottom of the valve element 20 stroke within the first tube; rather, the flange 68 contracts slightly when the male luer tip is urged against the valve element 20 to prevent such a seal from forming, thus eliminating the "back pressure wave" that has been found to be undesirable in designs with a wiper seal that is maintained during the entire stroke.

Figures 2B, 3B:
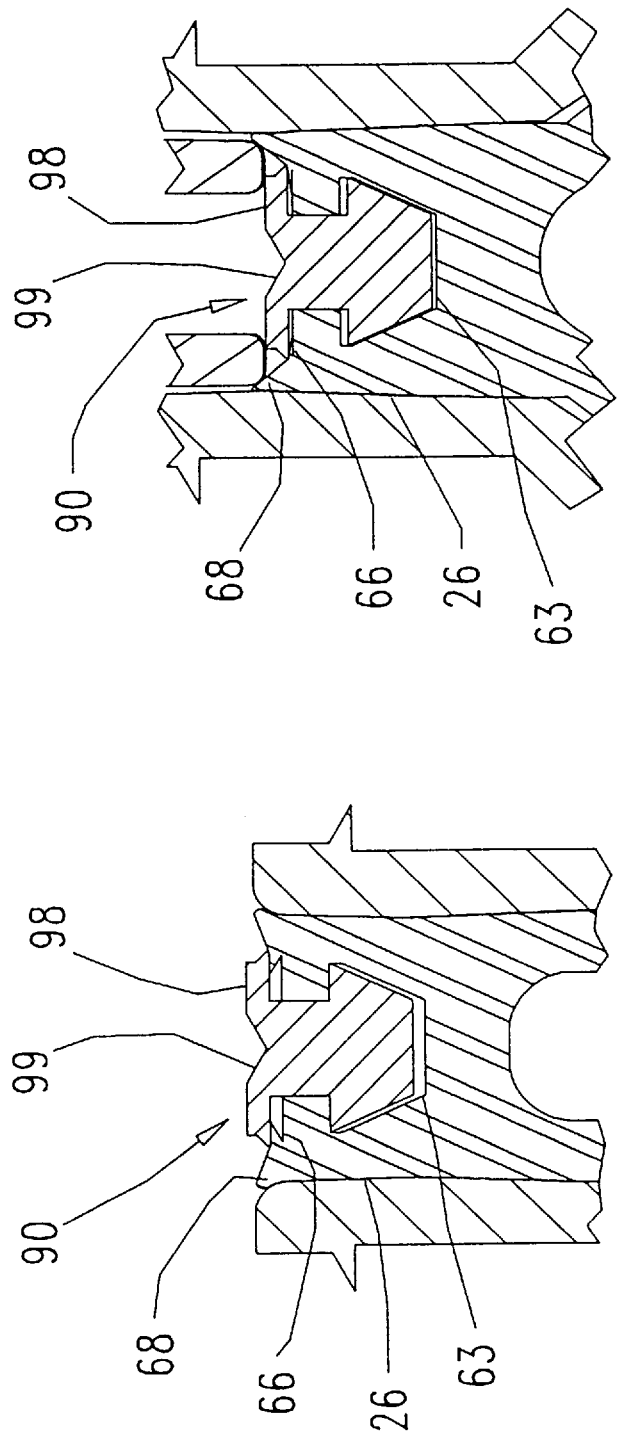
FIG. 2B shows a side elevation of a detail of the valve element of a first embodiment of the present invention with the valve element in the closed position.
FIG. 3B shows a side elevation of a detail of the valve element of a first embodiment of the present invention with the valve element in the open position.

As the valve element 20 is urged downward by the luer 110, the flared portion 72 and the concave wall 71 deform and invert, no longer touching the inner wall 30, as shown in FIG. 3B. This inversion breaks the seal to permit fluid passage. The lip 78 is maintained in place between the first and second tubes 14 and 18 so that the entire valve element 20 does not move downward. The flared portion 72 stretches upon inversion, thereby opening slits 82 and creating a fluid passageway from the luer 110 through the valve assembly 10 and out the opening 46.

The boss 80 is pivoted from its original position to where the underside 81 contacts the inner wall 43. The boss 80 prevents air bubbles from forming in the corner formed by the inner wall 43 and the angled portion 76 when fluid is passing within the third passageway 44.

The concave wall 71 and the flared portion 72 provide an elastic spring-like force biasing the valve element 20 in the upward position and requiring some degree of force to move the valve element 20 downward into the open position, thus permitting fluid flow. The resting position of the valve element 20 is in the upward, closed position. The upward bias maintains the positive fluid seal between the valve element 20 and the first tube 14 at the top surface and inner wall 30. The upward bias of the wall 71 and the flared portion 72 urge the return of the valve 10 to the closed, sealed position when the luer is withdrawn from the valve 10.

An advantage of this embodiment is that the wiper seal is eliminated, thus eliminating the pumping and back pressure wave noted above as being present in the prior art devices. Additionally, the inner protruding annular boss reduces the corner dead space, minimizes the area in which air bubbles can become trapped, and minimizes the overall design. The top surface can be wiped with an alcohol or similar wipe, yet the valve is maintained in a sealed configuration until a luer is inserted.

The use of the mated beveled portions of the valve element 20 and the plug 90 facilitate rapid snap fit assembly, eliminates welding or gluing of these two parts, and thereby reduces manufacturing costs.

A second, alternative, embodiment of the present invention is shown in FIGS. 7–10, in which a valve assembly 310 comprises a valve body 312 which is made of a first tube member 314 and a second tube member 318. A valve element 320 is slidingly disposed with the body 312. The first and second tube members 314 and 318 are made of a rigid material, such as that described in the first preferred embodiment.

The first tube member 314 comprises a cylindrical housing having a first portion 322 and a second portion 324. The inner wall 326 of the first end 322 is sized as a tapered female luer bore and forms a first passageway 328. A second portion 330 of the first tube member 314 extends downward and widens gradually at inner wall 333 forming a second passageway 332 (not shown). The bottom end 324 terminates in a lip 334. The inner wall 326 of the first passageway 328 functions as a secondary valve sealing surface when in contact with the valve element 320 in the closed position until the valve element 320 completely enters the second passageway 332.

The second tube member 318 comprises a cylindrical housing having a top end 340, a base ledge 341 and a bottom end 342 with a bore extending therethrough having an inner wall 343 defining a third passageway 344. The bottom end 342 has an opening 346 and can optionally have a male luer fitting 348 associated therewith in fluid communication with the passageway 346. The male luer fitting 348 can be connected to an external thread on a separate connector. Alternatively, the bottom end 342 can be adapted to be fitted to or to be an integral part of a tubing in a Y-site, multiple manifold, or other configurations, as described in detail in the referenced co-pending application. The top end 340 has a raised shoulder 350 sized to facilitate mating with the bottom end 324 of the first tube member 314.

Figure 7:
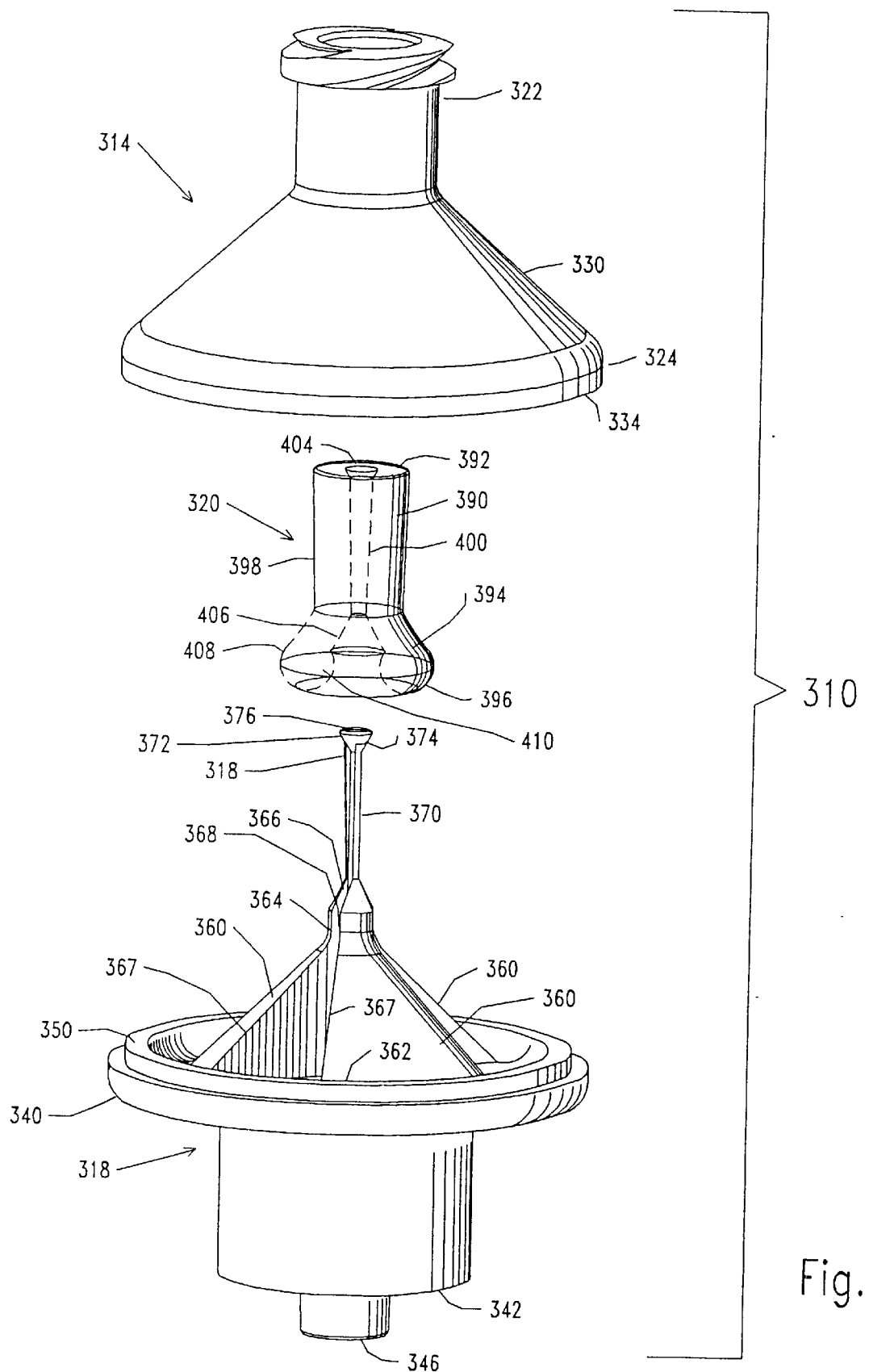
FIG. 7 shows an exploded perspective view in partial cutaway of a second embodiment of the present invention.

At least one, and preferably a plurality of wedge shaped ribs 360 extend upward from the base ledge 341, as shown in FIG. 7. The ribs 360 have a curved base 362 and taper upward to a generally straight segment 364 (with respect to the second tube member 340 axis) and terminate in a tapered end stop 366. The ribs have a side wall 367. Between each pair of opposing side walls 367 is defined a space 368. A pin 370 extends upward from the stop 366 and terminates in a stop 372, which has a beveled portion 374 and a top surface 376. The pin also has at least one, and preferably, a plurality of longitudinal grooves 378 which are in fluid communication with the spaces 368. The spaces 368 are in fluid communication with the passageway 344. The second tube 318, pin 370 and ribs 360 are preferably formed as a single piece. While the pin 370 has been described as having ribs and grooves therebetween, it should be understood that the pin can alternatively be hollow with a bore and apertures along the length of the pin 370 which function as fluid passageways.

The valve element 320 comprises an upper portion 390 having a top end 392, a middle portion 394 and a lower portion 396. The upper portion 390 has a slightly tapered outer wall 398 and preferably a slightly tapered inner wall 400 which defines a passageway 402. The top end 392 has a beveled opening 404. The middle portion 394 flares outward with respect to the upper portion 390 and has an inner wall 406 and outer wall 408 that are generally parallel to one another and terminates in the toroidal shaped lower portion 396. Preferably, the toroid has a bulbous rim 410, which projects inward with respect to the straight portion just below the beveled stop 366. The beveled portion 374 of the stop 372 forms a seal with the beveled opening 404 when in the closed position. This particular seal is broken when the luer tip (as described in detail hereinbelow) is pressed downward partially into the inner passageway 328.

The valve element 320 is made of an elastic material similar to the material described above with respect to the valve element 20.

To assemble the valve assembly 310, the valve element 320 is slid over the pin 370 so that the inner wall 406 rests on the stop 366 and the top surface 376 is generally even with the top end 392 of the valve element 320. Preferably, the top surface 376 extends slightly above the top end 392 to provide a centering rim target for easier alignment and insertion of the luer. The first tube 314 is placed on top of the second tube 318 so that the lip 334 mates with the raised shoulder 350 and sealed as described hereinabove. The valve element 320 can slide up and down over the pin 370. It is to be understood that this second embodiment can be modified to assemble as a snap fit device, as described in the first embodiment hereinabove.

After the assembly as described hereinabove has been completed, the valve assembly 310 is in a closed or sealed formation, with several points of seal being created. The beveled opening 404 in the top end 392 is sealed by the beveled portion 374 of the stop 372. This seal prevents contaminants from entering the valve assembly 310. The top end 392 is wipable by a convention alcohol or other cleaning means. The passageway 328 is sealed by the outer wall 398 of the upper portion 390 being in contact with the inner wall 326. This seal is maintained until the luer 420 in inserted completely within the inner passageway 328 and the valve element 320 is in the down position within the second passageway 332.

To break the seals, a standard male luer syringe 420 (or other device), having a tip 422 and an inner wall 424, is placed in contact with the top end 392. The elastic nature of the valve element 320 will resist downward movement. As the tip 422 is urged downward against the top end 392, the valve element 320 moves downward. As it does so, the seal between the stop 372 and the opening 404 is broken and a small amount of fluid can enter the inner passageway 402, travel down the grooves 378, enter the spaces 368 and exit the assembly 310 through the opening 346. It may be desirable to have a partial insertion of the luer tip 422 into the passageway 328 when a user wants to pre-flush the valve assembly with a small amount of fluid, or to remove a small amount of fluid, without creating a full passageway.

Figures 8, 9:
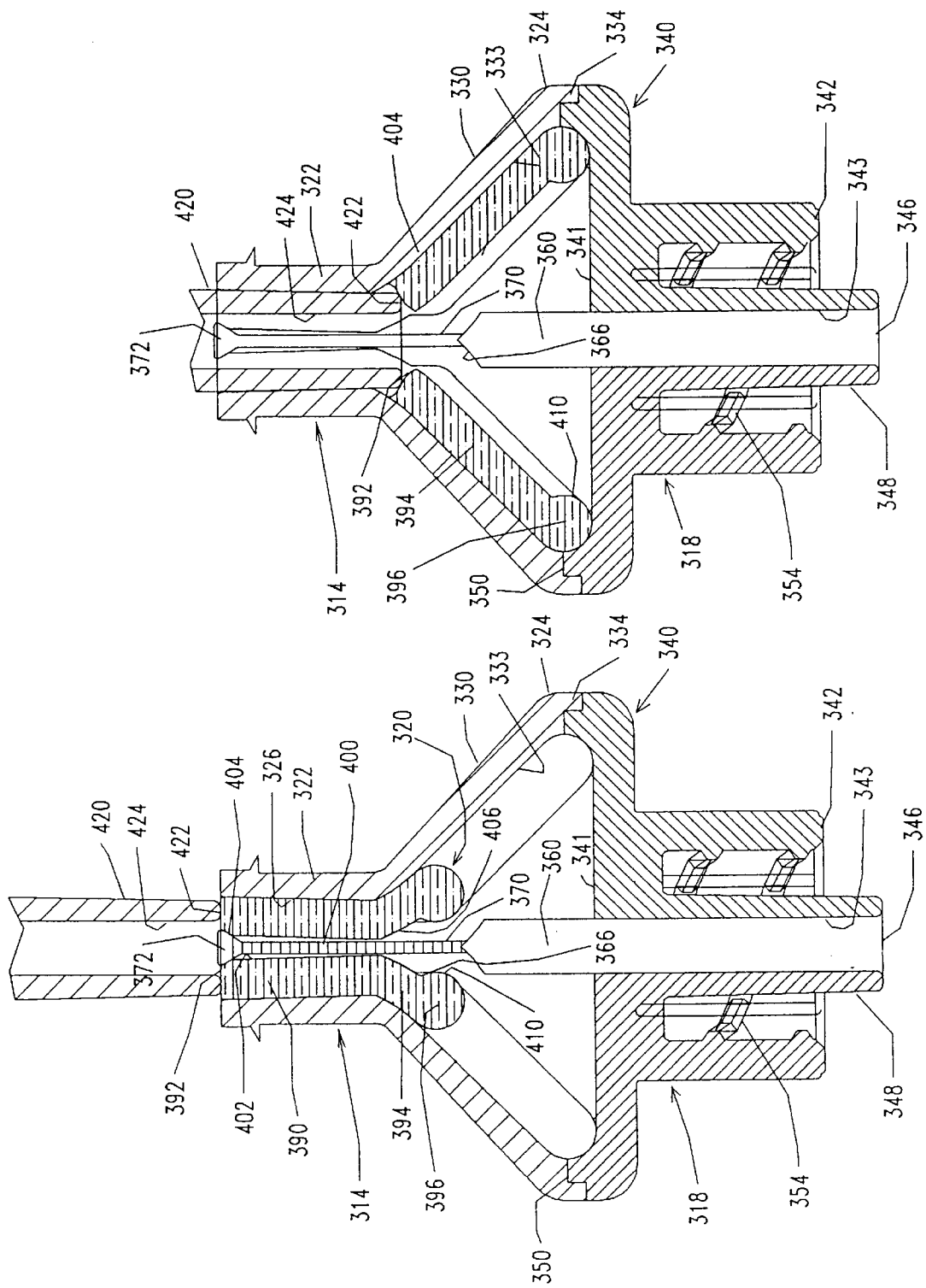
FIG. 8 shows a side elevation in cutaway of a second embodiment of the present invention with the valve element in the closed position.
FIG. 9 shows a side elevation in cutaway of a second embodiment of the present invention with the valve element in the open position.
Figure 11:
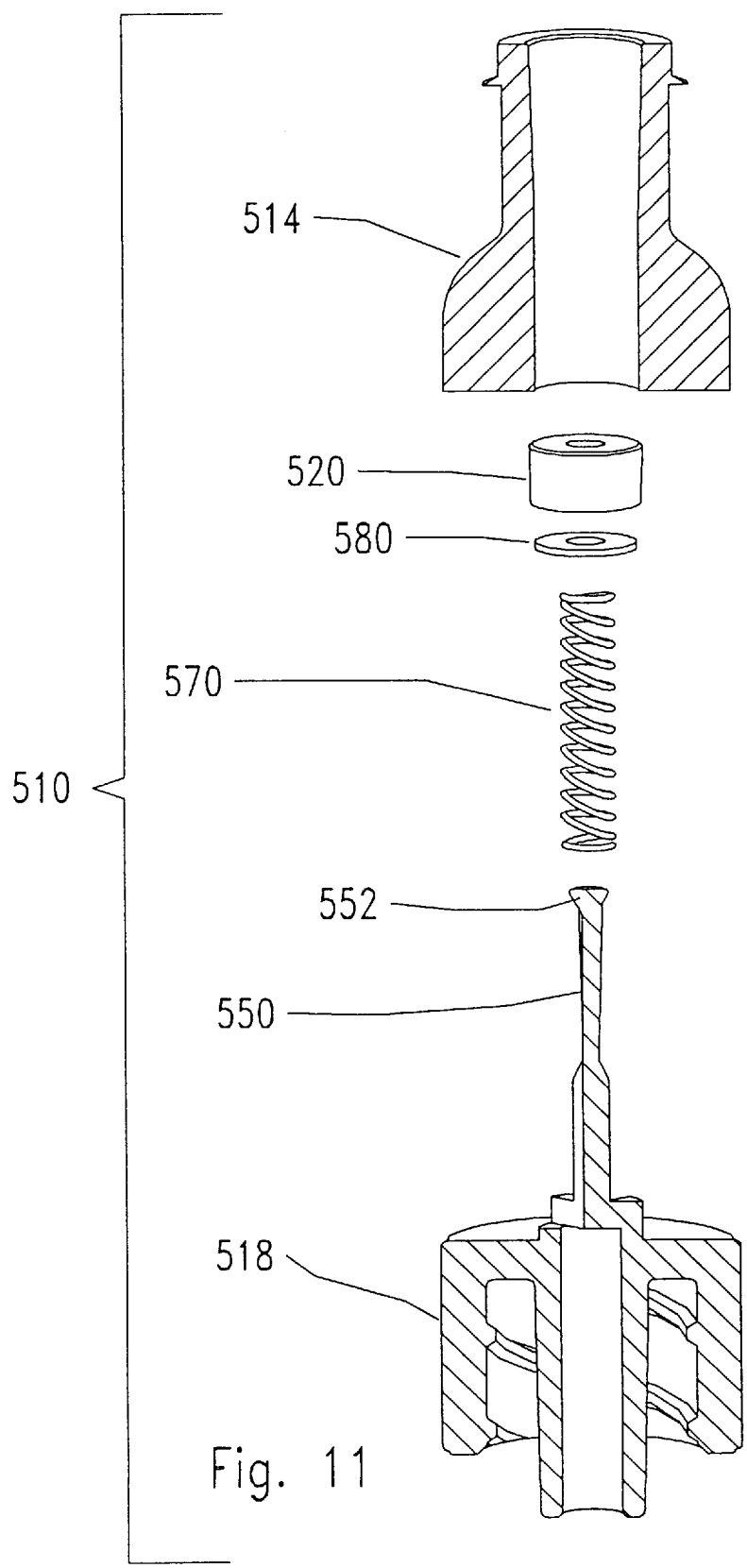
FIG. 11 shows an exploded perspective view in partial cutaway of a third embodiment of the present invention.
Figure 12:
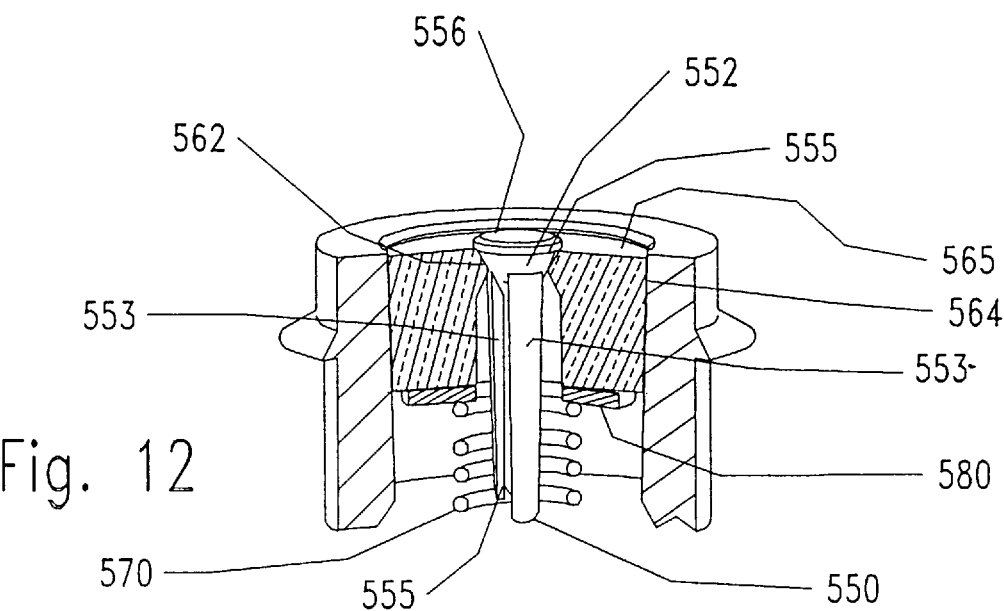
FIG. 12 shows a perspective view in partial cutaway of a detail of the valve element, spring pin assembly of a third embodiment of the present invention.
Figure 13:
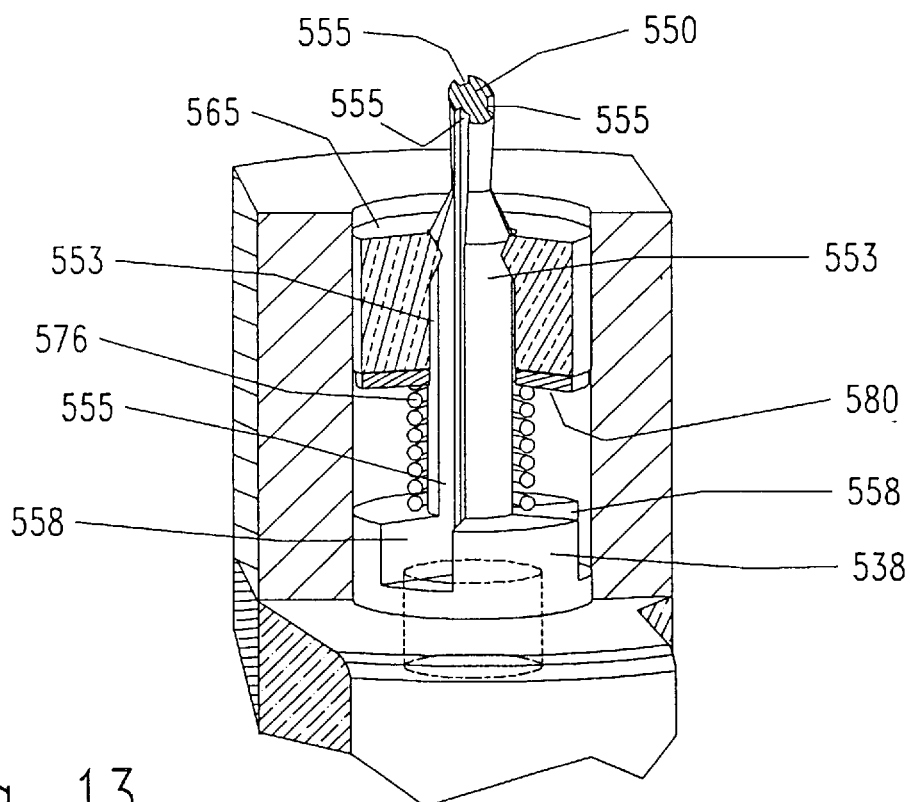
FIG. 13 shows a perspective view in partial cutaway of a detail of the valve element, spring and pin assembly of a third embodiment of the present invention.

As the luer tip 422 is urged downward, the seal is maintained between the inner wall 326 and the outer wall 398 until the luer is completely inserted. However, partial fluid flow occurs as soon as the seal between the stop 372 and the beveled opening 404 is broken. This novel configuration substantially reduces the possibility of a back pressure wave that can occur in conventional valves that have a wiper seal or other mechanism that maintains a fluid seal from top to bottom of the valve element "stroke." The partial fluid flow is made possible by the passageways created by the grooves 378. The toroidal lower portion 396 moves downward and outward and stretches over the ribs 360. The pin 370 enters the luer passageway 424. The lower portion 396 reaches its maximum downward and outward movement at the curved part of the raised shoulder 350, as shown in FIG. 9. At the maximum downward position the valve element 320 no longer contacts the ribs 360 except for the bulbous rim 410, thereby permitting full fluid flow within the spaces 368. Fluid can flow through the spaces 368 that begin at the straight segment 364 and continue downward toward the base ledge 341, and continue through the passageway 344 and out the opening 346. Once the lower portion 396 reaches its maximum downward and outward movement, more flow is allowed through the ribs 360. The valve element 320 is maintained in this orientation so long as a luer tip 422 is in the first tube 314. As the luer tip 422 is withdrawn, the valve element 320 moves upward due to elastomeric "memory," until the opening 404 moves upward to and becomes sealed against the stop 372.

One advantage of this embodiment is that the valve element creates a self-purging valve assembly. When the toroidal shaped lower portion 396 is pushed downward, it pushes air and fluid downward through the grooves 378, thereby minimizing or eliminating the air that may be trapped in the grooves 404.

A second advantage is that dead space is minimized, reducing the volume available in which air bubbles can form.

An advantage of both the first and second embodiments is that the designs permit for partial fluid flow and full fluid flow, depending on the degree of insertion of the luer into the valve body. It may be desirable for a user to withdraw a small amount of fluid from the valve while inserting a needle or syringe into the valve. Alternatively, it may be desirable to inject a small amount of fluid into the valve while withdrawing the needle, or to flush the assembly and/or the tubing prior to injection of other fluid. An example of this is when one is withdrawing a luer syringe from the valve assembly, a small amount of suction force may be created by the upward movement of the valve element. This suction force may draw a small amount of blood or other fluid into the valve assembly.

A fourth advantage is that the cost of manufacture and assembly are reduced because there are only three parts: the first tube 314, the second tube 318 and the valve element 320.

A fifth advantage is that the projecting pin protuberance 376 slightly above the top surface 392 presents a centering target for inserting the luer 420 into the valve 310.

A third, alternative, embodiment of the present invention is shown in FIGS. 11–16, in which a valve assembly 510 comprises a valve body 512 which is made of a first tube member 514, a second tube member 518, and a valve element 520 slidingly disposed with the body 512. The first and second tube members 514 and 518 are made of a rigid material, such as that described in the first preferred embodiment.

The first tube member 514 comprises a generally cylindrical housing having a top end 522, a bottom end 524, and an inner tapered passageway 526 defined by an inner wall 528. The outer wall 530 has an upper portion 532 having a generally straight wall extending downward to a lower portion 534 preferably having a wider diameter than the upper portion 532, the upper and lower portions connected by an intermediate rounded hip portion 536.

The second tube member 518 comprises a generally cylindrical housing having a central raised base support 538, an outer lip 540, to which the bottom end 524 of the first tube member 514 can be mated, a bottom end 541 and a bottom opening 542. Preferably, the bottom opening 542 is integral with a male luer fitting 544 associated therewith. It is to be understood that other tubes or fittings can be associated with the bottom opening, as described in the second embodiment hereinabove.

A pin 550 extends upward from the base support 538 and terminates at its distal end at a stop 552. The stop 552 preferably has a flared beveled terminus 554 and a generally flat top surface 556. The pin 550 has at least one, and preferably, a plurality of wedge-shaped (when viewed from a top view, as in FIG. 16) longitudinal ribs 553 extending from and around the circumference of the pin 550. The walls of the ribs 553 form a series of longitudinal grooves 555. The base support 538 has a space 558 associated with each groove 555 and the space and the groove are in fluid communication with the bottom opening 542. The pin 550 has an upper portion 557 and a lower portion 559 connected by a beveled portion 559A, the lower portion 559 has a larger diameter than the upper portion 557.

A valve element 520 comprises an elastic, deformable tube segment having a generally cylindrical shape. The valve element 520 is preferably made of silicone rubber, or other material similar to the valve elements 20 and 320 described hereinabove. The valve element 520 has an inner passageway 560 created by an inner wall 561 that is slightly tapered, a beveled top opening 562 and a bottom opening 563 as well as an outer wall 564 and a top surface 565.

A compression spring 570 having a diameter greater than the largest diameter portion of the pin 550 is capable of being slid over the pin. The spring 570 has a length shorter than that of the pin 550, when the spring 570 is in its extended configuration. The spring 570 can be made of plastic, metal or other insert, flexing material. Other biasing means can be used in place of the spring, such as a polyurethane cylinder or die spring, disc spring, S-shaped or cone-shaped segment of springlike material. When the valve is assembled and the valve element 520 is in the closed position, the spring 570 is is slightly compressed, placing an upward bias on the valve element 520, as described in further detail hereinbelow.

A washer 580 having an aperture 582 (not shown) defined therein can similarly slide over the pin 550. The washer aperture 582 is preferably narrower than the diameter of the spring 570 and serves to prevent the spring 570 from digging into the bottom of the valve element 520. The washer 580 can be made of plastic, Teflon, polycarbonate or other inert materials.

The spring 570 is first slid over the pin 550. Then the washer 580 is slid over the pin 550 so that it rests on top of the spring 570. The valve element 520 is forced over the stop 552 so that the beveled opening 562 contacts the bevel of the stop 552. Preferably, the top surface 556 extends slightly above the top end 522 to provide a centering rim target for easier alignment and insertion of the luer.

The first tube member 514 is lowered over the valve element 520 and mated with the lip 540 on the second tube member 518. The first and second tube members 514 and 518 are attached using glue, sonic, heat or chemical welding, fusing or the like. Any method of joining two mating surfaces that produce a fluid leak tight seal can be utilized. The tube members 514 and 518 can also be formed as discussed in the first embodiment with a snap fit lip and groove. It is to be understood that this third embodiment can be modified to assemble as a snap fit device, as described in the first embodiment hereinabove. With device assembled, the spring is maintained in a slightly compressed state, placing an upward force on the washer 580 and the valve element 520. This upward force maintains the positive seal between the valve element 520 and the inner wall 528 of the first tube member 514.

In its closed position the valve assembly 510 is sealed from contamination by the seals created between the beveled top opening of the valve element 520 and the stop 552, as well as the outer wall 564 of the valve element 520 and the inner wall 528 of the first tube member 514. The spring 570 maintains the valve element 520 biased upward to create the seals while in the closed position.

A male luer 590 having a tip 592 and an inner wall 594 can contact the top surface 565 of the valve element 520. As the luer 590 is urged downward, as shown in FIG. 15, the valve element 520 is urged downward and the spring 570 compresses against the base support 538, breaking the seal between the beveled top opening 562 of the valve element 520 and the flared stop 552. At this point a passageway is created by the luer 590, the inner passageway 560 in the valve element 520, and the grooves 555, which connect with the space 558 in the base support 538 and the bottom opening 563, thus allowing for a partial flow of fluid through the valve assembly 510.

As the luer 590 is urged further downward the luer tip 592 becomes fully engaged and the valve element 520 is in the full open position. In this open position, the inner passageway 526 of the valve element 520 also expands slightly under the downward force and the wider diameter of the base of the pin 550, creating a larger opening for fluid passage. When the luer 590 is removed, the spring 570 returns to the initial position, urging upward the valve element 520 and washer 580, which again forms a seal between the stop 552 and the beveled top opening 562.

An advantage of this third embodiment is that, similar to the second embodiment discussed hereinabove, fluid flow is possible in a partial or full flow, depending on the amount of insertion of the luer 590 into the valve assembly 510. The flat top surface 565 of the valve assembly 510 presents a surface that is easily wiped and that is sealed from contaminants entering the passageway 526. The possibility of a back pressure wave being produced is eliminated because the fluid seal is broken upon partial insertion of the luer tip into the valve 510. Upon full insertion of the luer 590 a full fluid flow is achieved because diameter of the inner passageway 560 of the valve element 520 expands when the luer presses downward and stretches over the beveled portion 559A to the larger diameter of the lower portion 559 of the pin 550. Also, as with the previous embodiment, purging of the valve assembly 520 is possible by partially inserting the luer 590 into the inner passageway 526 and breaking the seal between the beveled top opening 562 and the stop 552. Moreover, air and fluid entrapment is minimized because of the flat surface presented by the washer 580 and the self-purging nature of the open piston movement; i.e., as the valve element 520 and washer 580 are urged maximally toward the base support 538, there is minimal dead volume in which air and fluid can become entrapped.

While the invention has been described in connection with certain preferred embodiments, it is not intended to limit the scope of the invention to the particular forms set forth, but, on the contrary, it is intended to cover such alternatives, modifications, and equivalents as may be included within the spirit and scope of the invention as defined by the appended claims.

Claimed is:

1. A method of selectively controlling fluid flow through a fluid access system, comprising:
providing an aliquot of fluid in a fluid transmitting device;
providing a valve assembly for selectively controlling fluid flow, said valve assembly comprising
a first rigid tube member having a top, a bottom, a first portion containing a first inner wall defining a first passageway having a first diameter, said first tube member also having a second portion extending axially from said first portion and containing a second inner wall defining a second passageway having a diameter greater than said first passageway,
a second rigid tube member having
a base portion,
at least one fluid passageway defined in said base portion,
at least two ribs extending upward from said base portion, the volume between said at least two ribs defining a fluid passageway in communication with said at least one fluid passageway defined in said base portion, and
a pin extending upward from said at least two ribs and having a proximal and a distal end, said pin having at least one longitudinal groove defined therein, said groove being in fluid communication with said fluid passageway defined in said base portion, said distal end of pin terminating in a protuberance having an outer wall defining a primary valve sealing surface,
said first and second tube members capable of mating engagement with axial alignment; and
a resilient valve element comprising a generally cylindrical elastic body having a top and a bottom and having an upper portion having an outer wall and an inner wall, a middle portion having an inner wall and a generally flared outer wall terminating in a toroidal shaped lower portion, said valve element having a fluid passageway defined axially therein sized to be able to slidingly receive said pin, and,
inserting said fluid transmitting device into said first passageway such that said valve element moves from a closed position to an open position permitting fluid flow through said valve assembly; and,
transmitting fluid through said valve assembly.

2. The method of claim 1, further comprising the step of withdrawing an amount of fluid from said valve while introducing said fluid transmitting device into said valve.

3. The method of claim 1, further comprising the step of introducing an amount of fluid from said valve while withdrawing said fluid transmitting device from said valve.

4. The method of claim 1, wherein said valve element can move from a closed position to a partially open position permitting partial fluid flow and to a fully open position permitting full fluid flow.

5. The method of claim 1, wherein said fluid transmitting device is partially inserted into said first passageway such that it moves said valve element away from said primary valve sealing surface exposing said pin groove for partial fluid flow.

6. The method of claim 5, wherein upon partial insertion of said fluid transmitting device said inner wall of upper portion of valve element moves away from said primary valve sealing surface creating an opening for partial fluid flow along said at least one pin groove, and upon complete insertion of said fluid transmitting device said valve element moves downward and stretches over said ribs such that the upper and middle portions of the valve element do not contact said ribs, thereby permitting full fluid flow within said fluid passageway defined by the volume between said at least two ribs.

7. The method of claim 6, wherein said pin is received by said fluid transmitting device as said fluid transmitting device is inserted into said first passageway of said first tube member and said valve element moves downward toward said base portion.

8. An automatic fluid control valve, comprising:
a first rigid tube member having a top, a bottom, a first portion containing a first inner wall defining a first passageway having a first diameter and defining a secondary valve sealing surface, said first tube member also having a second portion extending axially from said first portion and containing a second inner wall defining a second passageway having a diameter greater than said first passageway;
a second rigid tube member having
a base portion,
at least one fluid passageway defined in said base portion,
at least two ribs tapering upward from said base portion, the volume between said at least two ribs defining a fluid passageway in communication with said at least one fluid passageway defined in said base portion, and
a pin extending upward from said at least two ribs and having a proximal and a distal end, said distal end of pin terminating in a protuberance having a beveled outer wall defining a primary valve sealing surface, and
said first and second tube members capable of mating engagement with axial alignment; and
a resilient valve element comprising a generally cylindrical elastic body having a top wipable by cleaning means, a bottom, an upper portion having an inner wall with a top beveled surface, and having an outer wall that creates a seal with said first tube member inner wall when said valve is assembled, and a middle portion having an inner wall and a generally flared outer wall terminating in a toroidal shaped lower portion, said valve element having a fluid passageway defined axially therein sized to be able to slidingly receive said pin wherein said protuberance of said pin extends above said top of said valve element when said valve is assembled,
whereby said valve element is slidingly disposed within said tube members and can move from a closed position to a partially open position permitting partial fluid flow and to a fully open position permitting full fluid flow.

9. The valve of claim 8, wherein said valve element is movable between a closed position when said beveled surface forms a seal with said beveled wall of said protuberance, a partially open position when said beveled surface moves away from said beveled wall permitting partial fluid flow through said valve assembly, and a fully open position when said valve element stretches over said ribs at a maximum downward position and permits full fluid flow through said fluid passageway defined by said at least two ribs.

10. The valve of claim 9, wherein said upper and middle portions of said valve element have no contact with said at least two ribs when said valve element is positioned at a maximum downward position within said first and second tube members, thereby permitting full fluid flow within said fluid passageway defined by the volume between said at least two ribs.

11. The valve of claim 9, wherein each of said at least two ribs tapers upward to a generally straight portion and terminates in a tapered end stop, said pin extending upward from said tapered end stops.

12. The valve of claim 8, wherein said toroidal shaped lower portion has a bulbous rim which projects inward with respect to said at least two ribs.

13. The valve of claim 8, wherein said pin has at least one longitudinal grove defined therein, said groove being in fluid communication with said fluid passageway defined in said base portion.

14. The valve of claim 8, wherein said pin has an interior bore therethrough and has at least one aperture defined therein, said aperture being in fluid communication with said fluid passageway defined in said base portion.

15. An automatic fluid control valve, comprising:
a first rigid tube member having a top, a bottom, a first portion containing a first inner wall defining a first passageway having a first diameter and defining a secondary valve sealing surface, said first tube member also having a second portion extending axially from said first portion and containing a second inner wall defining a second passageway having a diameter greater than said first passageway;
a second rigid tube member having
a base portion,
at least one fluid passageway defined in said base portion,
at least two ribs extending upward from said base portion, the volume between said at least two ribs defining a fluid passageway in communication with said at least one fluid passageway defined in said base portion, and
a pin extending upward from said at least two ribs and having a proximal and a distal end, said pin having at least one longitudinal groove defined therein, said groove being in fluid communication with said fluid passageway defined in said base portion, said distal end of pin terminating in a protuberance having an outer wall defining a primary valve sealing surface,
said first and second tube members capable of mating engagement with axial alignment; and
a resilient valve element comprising a generally cylindrical elastic body having a top and a bottom and having an upper portion having an outer wall and an inner wall, and a middle portion having an inner wall and a generally flared outer wall terminating in a toroidal shaped lower portion, said valve element having a fluid passageway defined axially therein sized to be able to slidingly receive said pin.

16. The valve of claim 15, wherein said protuberance has a beveled side wall.

17. The valve of claim 16, wherein said protuberance has a generally flat top surface.

18. The valve of claim 15, wherein said top of said protuberance extends above said top of said first valve member top when said valve is assembled.

19. The valve of claim 15, further comprising a male threaded luer bore defined in said second tube member.

20. The valve of claim 15, wherein said at least two ribs are tapered from said base to said pin.

21. The valve of claim 15, wherein each of said at least two ribs tapers upward to a generally straight portion and terminates in a tapered end stop, said pin extending upward from said tapered end stops.

22. The valve of claim 21, wherein said toroidal shaped lower portion has a bulbous rim which projects inward with respect to said at least two ribs.

23. The valve of claim 21, wherein said middle portion has a generally flared inner wall which sealingly contacts said tapered end stops when said valve element is in a closed position.

24. The valve of claim 15, wherein said ribs have rounded edges.

25. The valve of claim 15, wherein said pin, base portion and ribs are made as a single piece.

26. The valve of claim 15, wherein said toroidal shaped bottom portion forms a seal with said inner wall of said first tube member when said valve element is in a closed position and is capable of permitting fluid to flow therethrough when said valve element is in an open position.

27. The valve of claim 16, wherein inner wall of said top of said valve element has a beveled surface.

28. The valve of claim 27, wherein said beveled surface forms a seal with said beveled wall of said protuberance when said valve element is in a closed position, and wherein said beveled surface moves away from said beveled wall permitting fluid to flow through said at least one pin groove when said valve element is in a partially open position, and wherein said valve element stretches over said ribs at a maximum downward position and permits fluid flow through said fluid passageway defined by said at least two ribs when said valve element is in a fully open position, said valve element being movable between said closed, partially open and fully open positions.

29. The valve of claim 27, wherein said valve element is movable between a closed position when said beveled surface forms a seal with said beveled wall of said protuberance, a partially open position when said beveled surface moves away from said beveled wall permitting fluid to flow through said groove within said pin, and a fully open position when said valve element stretches over said ribs at a maximum downward position and permits full fluid flow through said fluid passageway defined by said at least two ribs.

30. The valve of claim 29, wherein said top of said valve element is wipable by cleaning means.

31. The valve of claim 29, wherein said upper and middle portions of said valve element have no contact with said at least two ribs when said valve element is positioned at a maximum downward position within said first and second tube members, thereby permitting full fluid flow within said fluid passageway defined by the volume between said at least two ribs.

32. The valve of claim 15, wherein said outer wall of said upper portion of said valve element creates a seal with said first tube member inner wall when said valve is assembled.

33. The valve of claim 15, wherein said first passageway is a female luer opening which can mate with a male luer fitting when inserted therein.

34. The valve of claim 33, wherein said upper portion of said valve element has a generally tapered outer wall.

35. The valve of claim 15, wherein said upper portion of said valve element has a generally tapered inner wall.

* * * * *